United States Patent
Virtue

(10) Patent No.: US 8,199,168 B2
(45) Date of Patent: Jun. 12, 2012

(54) SYSTEM AND METHOD FOR 3D GRAPHICAL PRESCRIPTION OF A MEDICAL IMAGING VOLUME

(75) Inventor: Patrick Michael Virtue, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1046 days.

(21) Appl. No.: 11/274,660

(22) Filed: Nov. 15, 2005

(65) Prior Publication Data
US 2007/0127792 A1  Jun. 7, 2007

(51) Int. Cl.
*G09G 5/00* (2006.01)
(52) U.S. Cl. ......................................................... 345/642
(58) Field of Classification Search .................. 345/419, 345/642
See application file for complete search history.

(56) References Cited

U.S. PATENT DOCUMENTS

| | | | |
|---|---|---|---|
| 5,734,384 A * | 3/1998 | Yanof et al. ..................... 345/424 |
| 5,737,506 A * | 4/1998 | McKenna et al. ............. 345/582 |
| 6,195,409 B1 * | 2/2001 | Chang et al. ..................... 378/20 |
| 6,219,403 B1 * | 4/2001 | Nishihara ......................... 378/65 |
| 6,411,298 B1 * | 6/2002 | Goto et al. ..................... 345/427 |
| 6,844,884 B2 | 1/2005 | Balloni et al. |
| 6,898,302 B1 | 5/2005 | Brummer |
| 7,496,222 B2 * | 2/2009 | Mussack et al. .............. 382/131 |
| 7,668,285 B2 * | 2/2010 | Mukumoto ....................... 378/4 |
| 2002/0071599 A1 * | 6/2002 | Herget et al. .................. 382/131 |
| 2003/0018250 A1 * | 1/2003 | Trousset et al. ............... 600/425 |
| 2004/0070584 A1 * | 4/2004 | Pyo et al. ........................ 345/419 |
| 2004/0210403 A1 * | 10/2004 | Heigl et al. ...................... 702/32 |
| 2006/0058620 A1 * | 3/2006 | Sakas et al. .................... 600/407 |
| 2006/0153454 A1 * | 7/2006 | Grimme ......................... 382/181 |

* cited by examiner

*Primary Examiner* — Edward Martello
(74) *Attorney, Agent, or Firm* — McAndrews, Held & Malloy, Ltd.; Rick Wascher

(57) ABSTRACT

Certain embodiments of the present invention provide for a system for three-dimensional graphical prescription of an imaging volume including a user interface component, a reference image, and a three-dimensional representation of the imaging volume. The user interface component includes a display. The reference image is presented on the display. The representation of the imaging volume is presented on the display. The representation of the imaging volume is overlaid at least in part on the reference image.

16 Claims, 8 Drawing Sheets

FIG. 6A
FIG. 6B
FIG. 6C
FIG. 6D
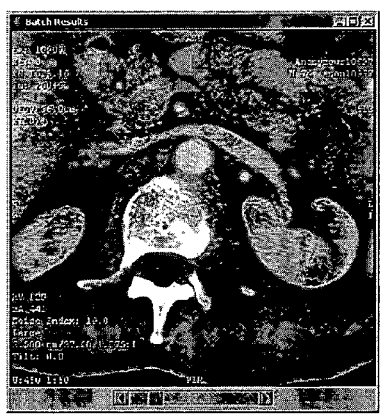
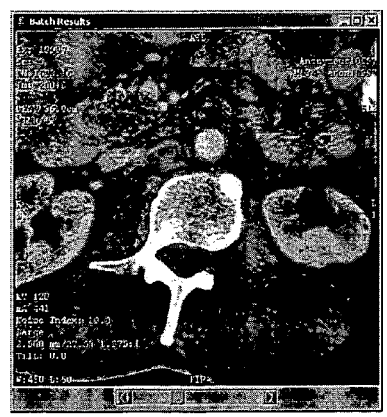

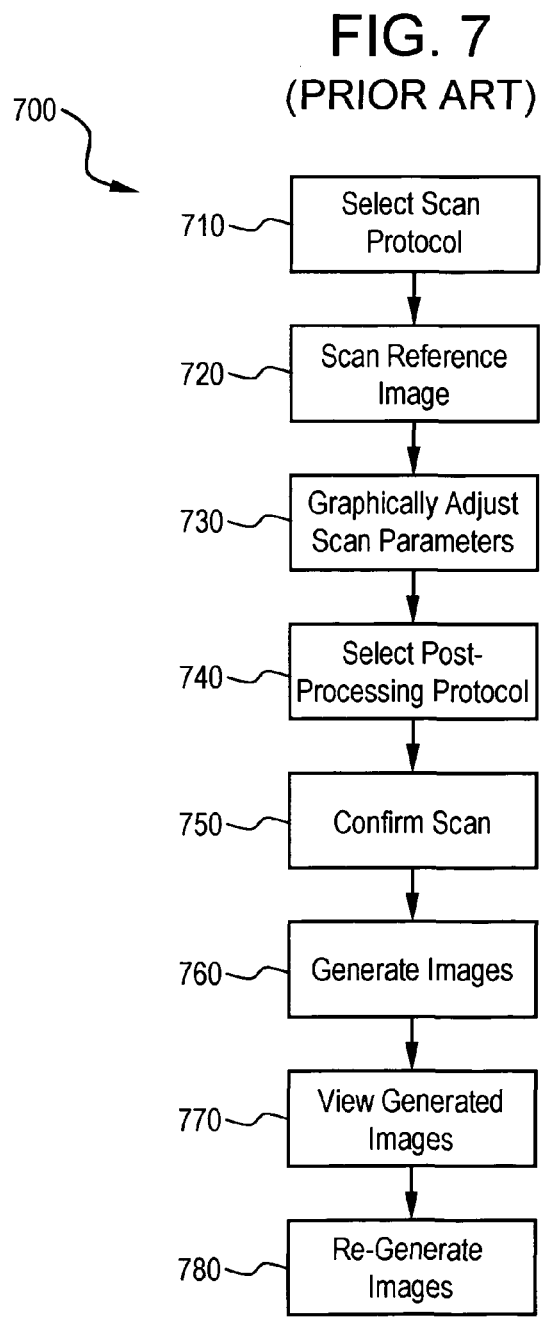

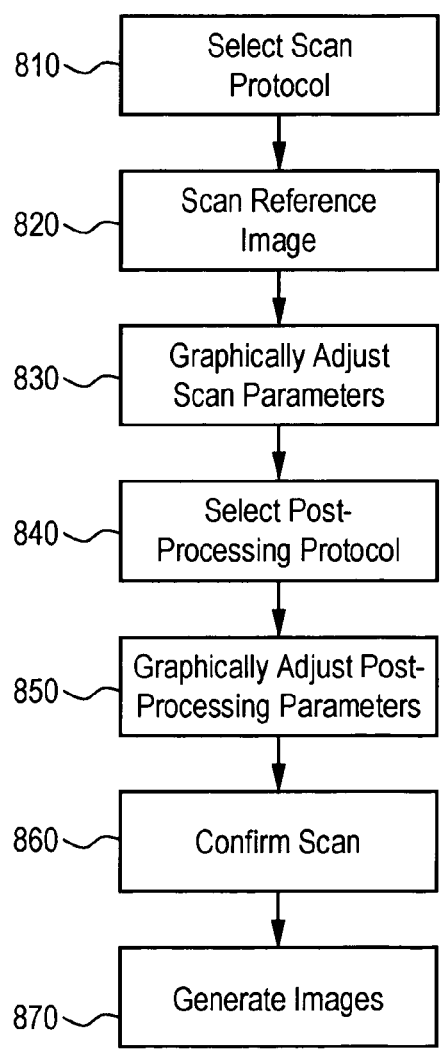

SYSTEM AND METHOD FOR 3D GRAPHICAL PRESCRIPTION OF A MEDICAL IMAGING VOLUME

RELATED APPLICATIONS [Not Applicable]

FEDERALLY SPONSORED RESEARCH or DEVELOPMENT [Not Applicable]

MICROFICHE/COPYRIGHT REFERENCE [Not Applicable]

BACKGROUND OF THE INVENTION

The present invention generally relates to graphical prescription in imaging systems. In particular, the present invention relates to a system and method for three-dimensional (3D) graphical prescription of a medical imaging volume.

Medical imaging systems may be used to capture images to assist a physician in making an accurate diagnosis. Imaging systems typically include a source and a detector. Energy, such as x-rays, produced by the source travel through an object to be imaged and are detected by the detector. An associated control or image processing system obtains image data from the detector and prepares a corresponding diagnostic image on a display.

Image data may come from a variety of sources. Images may have been generated and/or acquired from one or more imaging sessions and involve different modalities (e.g., ultrasound (US), magnetic resonance (MR), computed tomography (CT), x-ray, positron emission tomography (PET), nuclear, thermal, optical, video, etc.), views, slices, and/or protocols. Images may have originated from a single source or be a result of calculation (e.g., fused or compound images from multiple modalities).

An image processing system may combine image exposures with reference data to construct a 3D volumetric data set. For example, a 3D volumetric data set may be formed by combining successively scanned slices or planes of an object. For example, axial x-ray slices may be used to construct 3D volumetric data set.

A physician may then desire to view image slices in another plane. The 3D volumetric data set may be used to generate images, such as slices, or a region of interest from the object. For example, the image processing system may produce from the volumetric data set sagittal, coronal, and/or axial views of a patient's spine, knee, or other area. These image slices may then be generated from the 3D data set by a processing component, such as an image processing component, for example.

Graphical prescription is a mechanism by which a user, such as a physician, may prescribe the image slices to be generated. Generally, a reference image (also referred to as a scout image or a localizer image), or a set of reference images, is obtained from an imaging system and/or imaging component. The reference image(s) are then displayed to the operator. The operator may then mark on the reference images using, for example, lines or boxes to prescribe the desired image slices to be generated. The marks are overlaid on the reference image and depict the position and orientation of the images to be generated. An operator may then adjust the marks until the desired prescription is specified.

Efficient prescription is highly desirable. That is, it is desirable that an operator be able to quickly prescribe the images to be generated. In addition, it is highly desirable for an operator to be able to accurately prescribe the desired images because it may be time consuming to make several iterations of prescriptions and generate new images. However, it is frequently difficult for the operator to properly visualize the spatial location and orientation of the prescription, especially when imaging the interior of a three-dimensional structure. Oblique and double oblique prescriptions are particularly difficult for an operator to visualize and properly prescribe. The use of more than one reference image aids the user in visualizing the prescription, but 3D position and orientation are still difficult for operators to interpret across multiple reference images and, as a result, prescriptions are incorrect or prescriptions are not created until after the full scan has taken place.

Current systems may, as described above, overlay marks, such as lines, representing an image plane, on a two-dimensional (2D) reference image. The image to be generated is in the plane normal to the reference image, through the marked line. When multiple reference images are used that are non-orthogonal, the imaging plane can not be represented as a line on one or more of the reference images. Thus, an operator may have difficulty properly visualizing the image prescription. In addition, manipulating the prescription becomes more difficult and less intuitive. As a result, the generated images may not be optimal, requiring the operator to make another iteration of revising the prescription and re-generating the images.

Therefore, there is a need for a system and method for 3D graphical prescription of a medical imaging volume.

BRIEF SUMMARY OF THE INVENTION

Certain embodiments of the present invention provide for a system for three-dimensional graphical prescription of an imaging volume including a user interface component, a reference image, and a three-dimensional representation of the imaging volume. The user interface component includes a display. The reference image is presented on the display. The representation of the imaging volume is presented on the display. The representation of the imaging volume is overlaid at least in part on the reference image. In an embodiment, the imaging volume is presented on a plurality of reference images. In an embodiment, the imaging volume is oblique relative to the reference image. In an embodiment, the representation of the imaging volume is presented at least in part outside the plane of the reference image. In an embodiment, the representation of the imaging volume includes symbology for manipulating the imaging volume. Certain embodiments include a processing component. The processing component is in communication with the user interface component. The processing component generates a generated image based at least in part on the imaging volume. Certain embodiments include an imaging component. The imaging component is in communication with the user interface component. The imaging component acquires a scan image based at least in part on the imaging volume.

Certain embodiments of the present invention provide a method for three-dimensional graphical prescription including displaying a reference image on a display and presenting a three-dimensional representation of an imaging volume. The representation is presented at least in part overlaid on the displayed reference image. In an embodiment, the representation of the imaging volume includes symbology for manipulating the imaging volume. Certain embodiments include generating a generated image based at least in part on the imaging volume. Certain embodiments include determining automatically the orientation of the generated image. Certain embodiments include acquiring a scan image. The scan image is acquired at least in part by an imaging component. In an embodiment, the acquired scan image is acquired by the imaging component based at least in part on the imaging volume.

Certain embodiments of the present invention provide a method for improving imaging workflow including displaying a reference image, presenting a three-dimensional representation of an imaging volume, acquiring a scan image, and generating a generated image based at least in part on the imaging volume and the acquired scan image. The representation of the imaging volume is presented at least in part overlaid on the reference image. In an embodiment, the presenting step occurs at least in part during scan setup. In an embodiment, the scan image is acquired based at least in part on the imaging volume. In an embodiment, the reference image is acquired by a first imaging component. In an embodiment, the scan image is acquired by a second imaging component. In an embodiment, the imaging volume is initially defined by an imaging protocol.

Certain embodiments of the present invention provide a computer-readable medium including a set of instructions for execution on a computer. The set of instructions include a display routine and a user interface routine. The display routine is configured to display a reference image. The user interface routine is capable of overlaying a three-dimensional representation of an imaging volume on the reference image. The user interface routine is capable of adjusting the imaging volume based at least in part on input from a user.

BRIEF DESCRIPTION OF SEVERAL VIEWS OF THE DRAWINGS

FIGS. 6A-6D illustrate image slices generated from a graphical prescription in accordance with an embodiment of the present invention.

FIG. 7 illustrates a flow diagram for a method for graphical prescription in current systems.

FIG. 8 illustrates a flow diagram for a method for 3D graphical prescription in accordance with an embodiment of the present invention.

Figure 1:
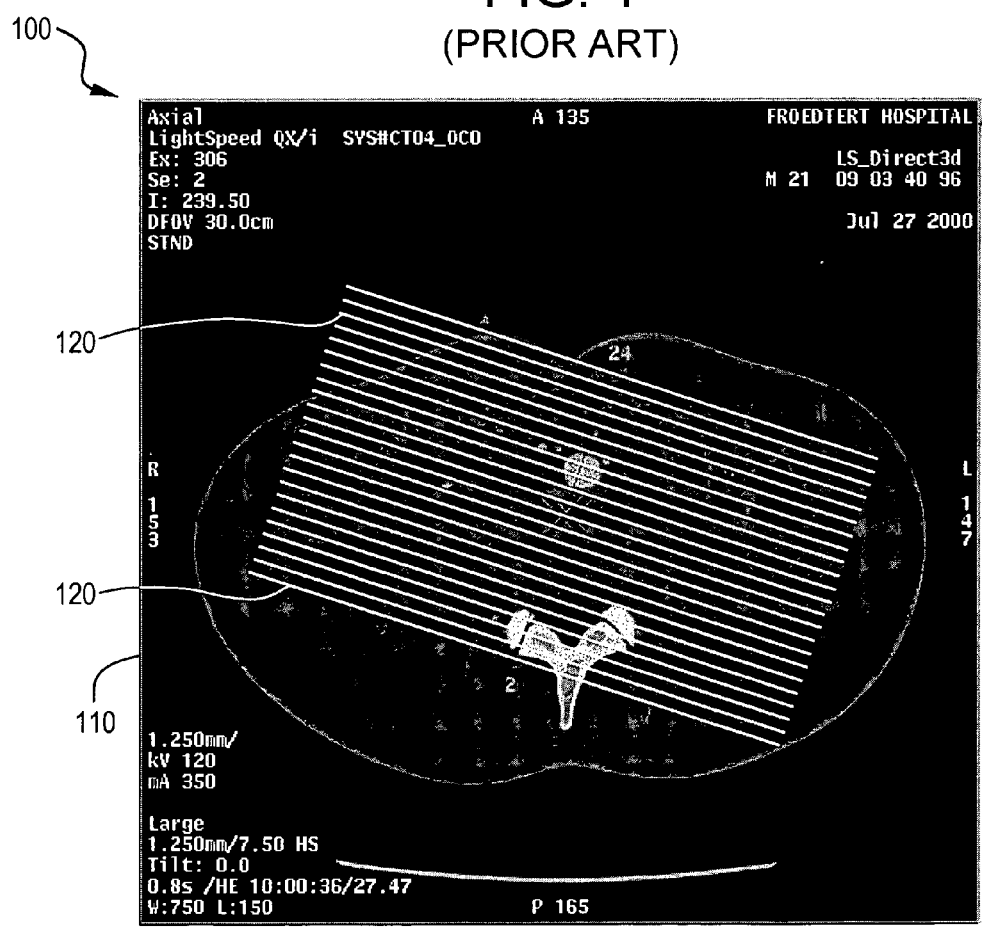
FIG. 1 illustrates a prior art graphical prescription interface.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

It is noted that the following is described primarily with reference to a computed tomography (CT) imaging system, although it would be appreciated by one of ordinary skill in the art that certain embodiments of the present invention may be applied to other imaging modalities. Other modalities may include, for example, ultrasound, magnetic resonance, x-ray, and positron emission tomography.

As discussed above, current systems for graphical prescription may utilize a set of marks, such as lines, on a reference image (also referred to as scout images or localizer images) to prescribe an imaging volume and/or a set of images to be generated. For example, FIG. 1 illustrates a prior art graphical prescription interface 100. The graphical prescription interface 100 includes a reference image 110 and one or more lines 120 representing the image slices to be generated. The prescribed images to be generated are normal to the plane of the reference image 110, and thus appear as lines 120 in the interface 100.

In the interface 100, the lines 120 are parallel to each other. Thus, the set of lines 120 may be viewed to define an imaging volume shaped as a rectangular prism. The imaging volume is bound on one axis by the planes depicted by the first and last lines 120 in the set. The imaging volume is bound on another axis by the plane defined by the edges of the lines 120. The third axis of the imaging volume, the one normal to the plane of the reference image 110, cannot be depicted by the interface 100.

Figure 2:
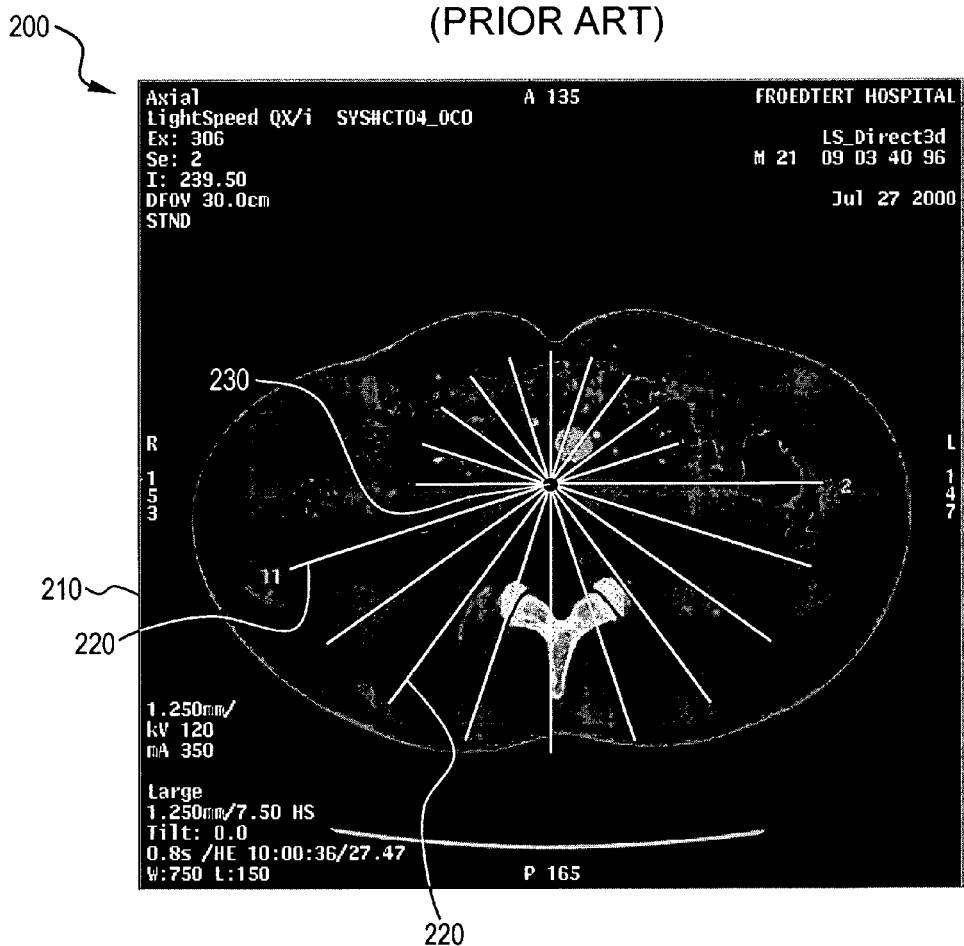
FIG. 2 illustrates a prior art graphical prescription interface.

FIG. 2 illustrates a prior art graphical prescription interface 200. The graphical prescription interface 200 includes a reference image 210 and one or more lines 220 representing the image slices to be generated. The prescribed images to be generated are normal to the plane of the reference image 210, and thus appear as lines 220 in the interface 200.

In the interface 200, the lines 220 all pass through a point 230. That is, the image slices to be generated, as represented by the lines 220, are revolved about the axis described by the point 230. When the midpoint of the point 230 is at the midpoint of the lines 220, the prescribed imaging volume is a cylinder. Similar to the volume described above in interface 100, one axis of the prescribed imaging volume (the axis running normal to the reference image 210 through the point 230) cannot be depicted by the interface 200.

Figure 3:
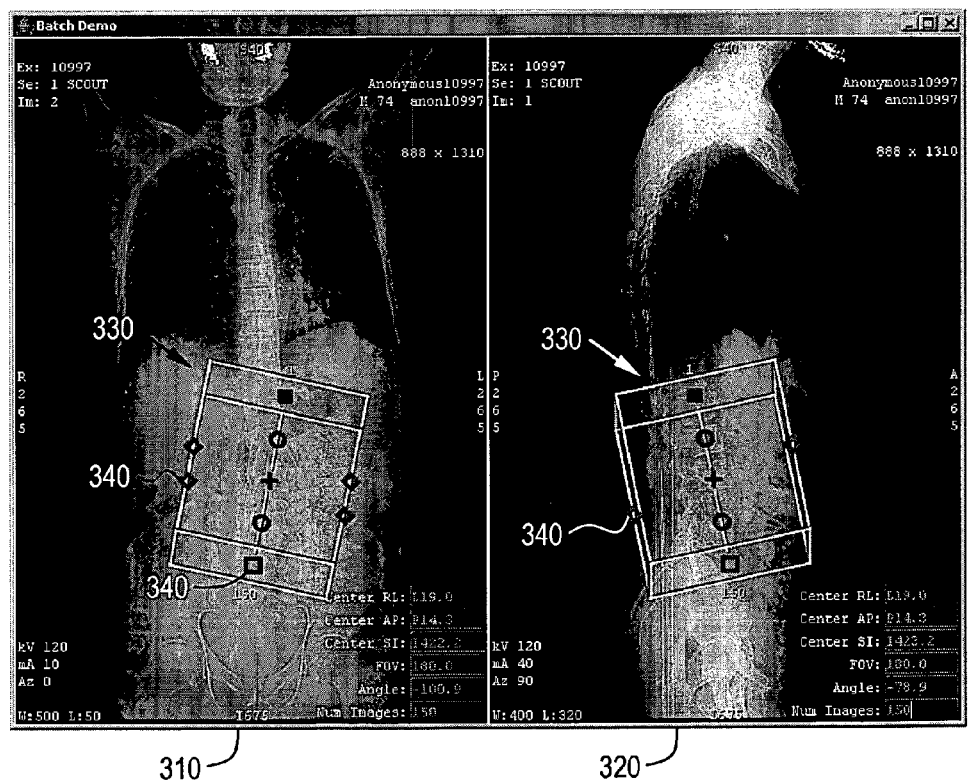
FIG. 3 illustrates a 3D graphical prescription interface in accordance with an embodiment of the present invention.

FIG. 3 illustrates a 3D graphical prescription interface 300 in accordance with an embodiment of the present invention. The interface 300 illustrated in FIG. 3 includes two reference images 310, 320 and a 3D representation 330 of an imaging volume. A representation 330 of the imaging volume is overlaid on each of reference image 310 and 320.

It should be understood that the interface 300 may include one or more reference images. That is, the interface 300 may include reference image 310 and/or reference image 320 and/or other possible reference images or combinations, for example. As another example, the interface 300 may include only reference image 310.

A reference image utilized in the interface 300 may be, for example, axial, sagittal, coronal, or oblique. A reference image may be generated and/or acquired by an imaging system and/or imaging component utilizing any of a number of imaging modalities. For example, a reference image may be a CT scout image. Alternatively, a reference image may be a PET volume maximum intensity projection (MIP). A reference image may be a 3D image representing a volume, such as, for example, a CT scout image. A reference image may be a 2D image representing a plane through the object being imaged, such as, for example, an MR slice.

The representation 330 of the imaging volume represents the imaging volume to be prescribed. That is, the representation 330 graphically illustrates the one or more of the parameters to be used to generate images. The parameters may include, for example, the position and orientation (see, e.g., FIG. 4, described below) of the imaging volume and the number of slices to be generated (see, e.g., FIG. 5, described below). Generated images may be generated from, for example, scan images based at least in part on the prescribed imaging volume. The representation 330 of the imaging volume may be oblique or double oblique with respect or relative to a reference image such as reference image 310.

In operation, an imaging system acquires one or more reference images. The following discussion will assume two reference images were acquired, although it would be appreciated by one of ordinary skill in the art that one or more reference images may be utilized. The reference images may be similar to reference image 310 and reference image 320, illustrated in FIG. 3. The reference images may be acquired from an imaging system; one or more imaging sessions; retrieved from an information management system (e.g., picture archiving and communication systems (PACS) or radiology information systems (RIS)); generated from views, slices, protocols; and/or the result of a calculation (e.g., fused or compound images from multiple modalities), for example. Reference images may be acquired from one or more modalities such as ultrasound, magnetic resonance, computed tomography, x-ray, or positron emission tomography, for example.

The reference images are displayed and/or presented to a user by a user interface component. The user interface component may be and/or may include a display, a computer monitor, television, or tablet computer, for example. The reference images are displayed using a graphical prescription interface such as interface 300. The interface 300 includes the reference images 310, 320 and a 3D representation 330 of an imaging volume.

The representation 330 of the imaging volume may be rendered in a variety of ways. For example, the representation 330 illustrated in FIG. 3 includes all 12 edges of the imaging volume, which is a rectangular prism. As another example, the representation 330 of the imaging volume may include only those edges "visible" to the user. That is, edges hidden by the volume may not be rendered in the representation 330. Other alternative representations are discussed in more detail below.

In certain embodiments, the imaging volume may be a cylinder or a polyhedron, for example. The imaging volume prescribes the image slices to be generated. The slices may be, for example, evenly spaced within the imaging volume. As another example, the user may specify the number, position and orientation of each slice or set of slices within the imaging volume. The imaging volume may be a complex polyhedron, for example, that approximates the volume occupied by a region of interest. For example, a complex polyhedron may be used to for an imaging volume covering the liver.

In certain embodiments, the interface 300 may include symbology, such as, for example, control points 340. The symbology may allow a user to, for example, adjust or manipulate the imaging volume illustrated by, for example, the representation 330. For example, the control points 340 of representation 330 may allow a user to manipulate the imaging volume represented by representation 330. A user may be able to alter the position, orientation, shape, and/or dimensions of the imaging volume, for example. For example, a user may utilize a control point to rotate the imaging volume about an axis so the volume is positioned to generate images for an area of interest. As another example, a user may use one or more control points to adjust the dimensions and positions of the imaging volume. The changes to the imaging volume will in turn be reflected in an updated representation 330 of the imaging volume. Thus, a user may graphically prescribe the imaging volume and see changes reflected immediately.

In embodiments, the imaging volume may extend beyond the boundaries of the reference image. For example, in the case of a 2D reference image, the imaging volume may extend beyond the plane of the reference image. In certain embodiments, the representation 330 of the imaging volume may be rendered outside of the plane of the 2D reference image. For example, the portion of the imaging volume "behind" the plane of the 2D reference image may be shaded. In an embodiment, the portion of the imaging volume "behind" the plane of the 2D reference image may not be rendered at all (i.e., truncated). In an embodiment, the portion of the imaging volume "in front of" the plane of the 2D reference image may be shaded, translucent, or truncated. In an embodiment, only the portion of the imaging volume that intersects the 2D reference plane may be rendered. In an embodiment, the representation 330 of the imaging volume may be projected onto the plane of the 2D reference image.

In certain embodiments, the interface 300 is in communication with a processing component. The processing component may generate generated images based at least in part on the prescribed imaging volume represented by the representation 330, for example. The generated images may be, for example, image slices.

In certain embodiments, the interface 300 is in communication with an imaging component. The imaging component may be an imaging system such as, for example, a CT scanner or an MR scanner. The imaging component may acquire scan images and/or reference images based at least in part on the imaging volume represented by the representation 330, for example.

Figure 4:
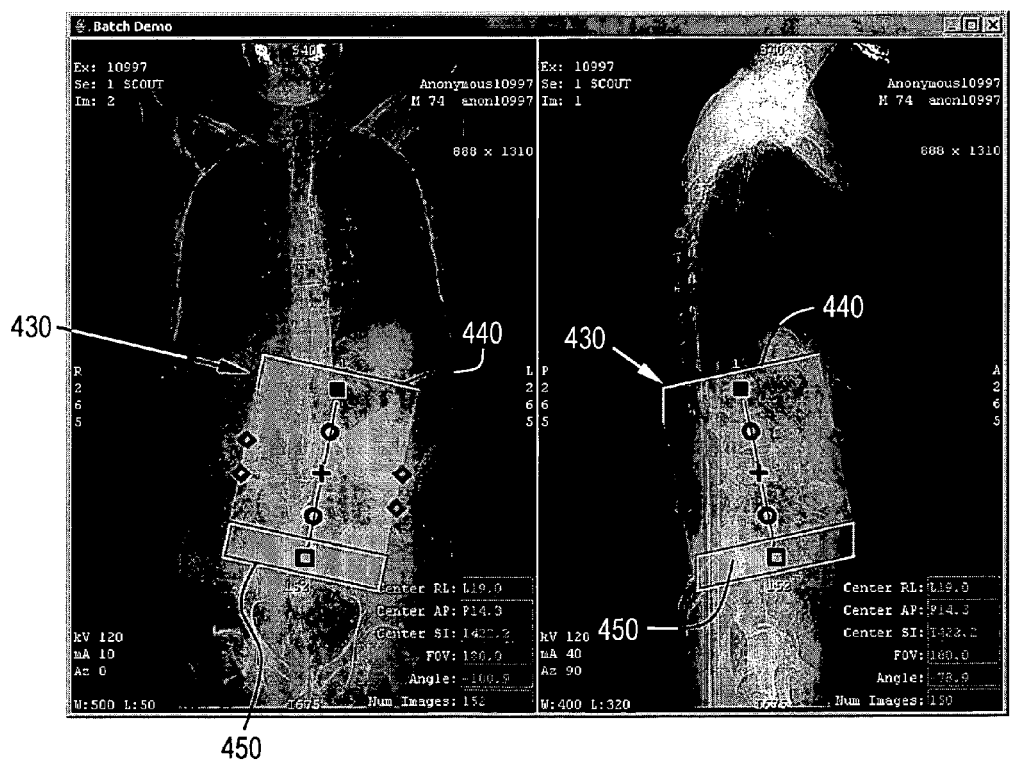
FIG. 4 illustrates a 3D graphical prescription interface in accordance with an embodiment of the present invention.

FIG. 4 illustrates a 3D graphical prescription interface 400 in accordance with an embodiment of the present invention. The interface 400 may be similar to the interface 300, described above. The imaging volume represented by representation 430 is similar to the imaging volume represented by representation 330 (i.e., a rectangular prism).

The representation 430 illustrated in FIG. 4 includes only the edges of the "top" 440 and "bottom" 450 of the representation 430 of the imaging volume that are "visible." That is, only two edges of the "top" 440 of the volume are rendered in the representation 430 because the other two edges would be "hidden" behind the volume. In contrast, the "bottom" 450 of the representation 430 of the imaging volume shows all four edges as that plane is "visible."

In certain embodiments, as illustrated in FIG. 4, the representation 430 of the imaging volume may include shading. The shading may be translucent or opaque coloring, for example. As another example, the shading may include a pattern of lines or dots. The shading may aid a user in visualizing the imaging volume.

Figure 5:
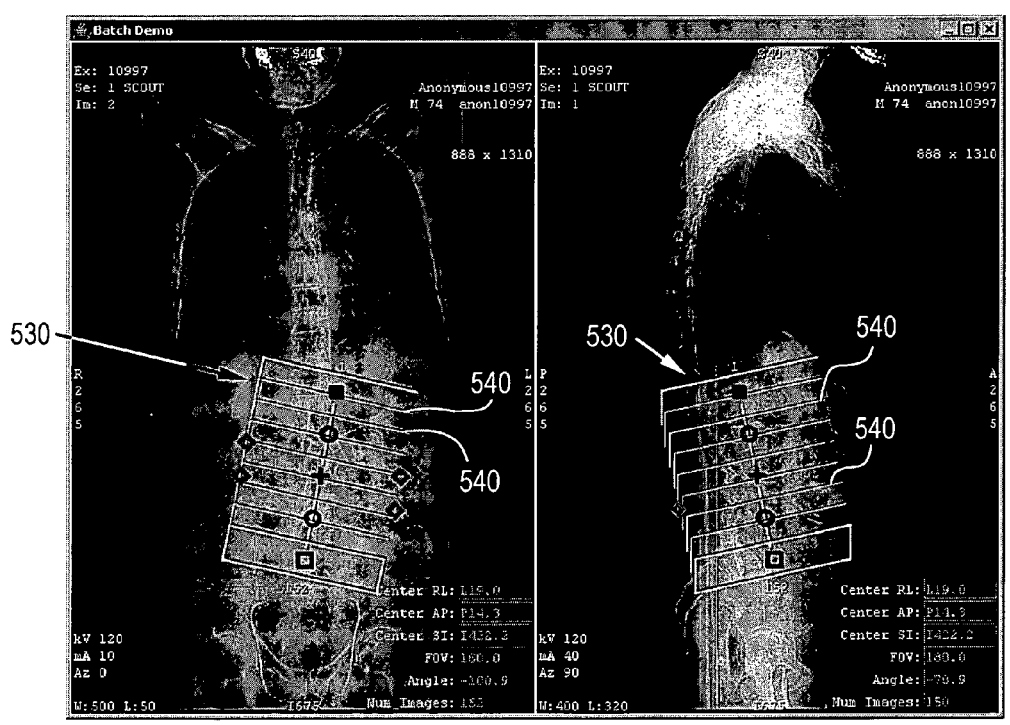
FIG. 5 illustrates a 3D graphical prescription interface in accordance with an embodiment of the present invention.

FIG. 5 illustrates a 3D graphical prescription interface 500 in accordance with an embodiment of the present invention. The interface 500 may be similar to interface 300 and/or interface 400, described above. The imaging volume represented by representation 530 is similar to the imaging volume represented by representations 330, 430, described above (i.e., a rectangular prism).

The representation 530 illustrated in FIG. 5 includes, similar to the representation 430 of the imaging volume described in FIG. 4 above, the edges of the "top" and "bottom" of the imaging volume that are "visible." The representation 530 also includes representations of the image slices 540 to be generated from the prescribed imaging volume. As with the "top" and "bottom" of the imaging volume, the representations of the image slices 540 include only the "visible" edges of those slices. Typically, the "top" and "bottom" of the imaging volume will also be generated as image slices. Thus, the representation 530 illustrates the stack of slices to be generated from the prescribed imaging volume.

In certain embodiments of the present invention, the user may switch between various representations of the imaging volume. For example, a user may begin by using a representation of the imaging volume similar to representation 330 (described above) for coarser positioning of the volume. The user may then utilize a representation similar to representation 530 (described above) to more finely and/or accurately prescribe the imaging volume and specify the desired image slices to be generated.

Components and/or functionality of the interfaces 300, 400, 500 may be implemented alone or in combination in hardware, firmware, and/or as a set of instructions in software, for example. Certain embodiments may be provided as a set of instructions residing on a computer-readable medium, such as a memory or hard disk, for execution on a computer or other processing device, such as, for example, a PACS workstation or image viewer.

FIGS. 6A-6D illustrate image slices generated from a graphical prescription in accordance with an embodiment of the present invention. For example, FIGS. 6A-6D may correspond to the first four image slices represented in the representation 530 of the imaging volume illustrated in FIG. 5, described above.

FIG. 7 illustrates a flow diagram for a method 700 for graphical prescription in current systems. First, at step 710, a scan protocol is selected. Then, at step 720, a reference image is scanned. Next, at step 730, scan parameters may be graphically adjusted. At step 740, a post-processing protocol is selected. Then, at step 750, the scan is confirmed. Next, at step 760, images are generated. At step 770, the generated images are viewed. Then, at step 780, images are re-generated. The method 700 is described with reference to elements of systems described above, but it should be understood that other implementations are possible.

First, at step 710, a scan protocol is selected. A scan protocol may, in part, configure an imaging system for a particular type of scan. A user may select a scan protocol based on, for example, an order specific to a patient regarding a region of the body to be scanned. For example, a patient may come to the imaging department of a medical facility with an order for a liver scan. A scan protocol may then be selected which configures the imaging system for the appropriate scan.

Then, at step 720, a reference image is scanned. The imaging system then scans one or more reference or scout images. The reference image(s) are presented to the operator on a display, for example. The reference image may be, for example, a CT scout image.

Next, at step 730, scan parameters may be graphically adjusted. The operator then graphically adjusts the scan parameters, if necessary. The operator may graphically adjust the scan parameters by adjusting, for example, lines bounding the region to be scanned displayed on the reference image. The scan parameters may need to be adjusted if, for example, the parameters do not align the area to be imaged correctly for the specific patient.

At step 740, a post-processing protocol is selected. The operator selects a post-processing protocol. Alternatively, the post-processing protocol may be specified as part of the scan protocol. For example, the post-processing protocol may prescribe an imaging volume to generate image slices for. In current systems, the parameters for generating new images cannot be checked and/or visually adjusted at this point.

Next, at step 750, the scan is confirmed. The operator confirms the scan and the imaging system then acquires scan images. This process may take a relatively long period of time, depending on the imaging modality. For example, the scan and reconstruction of CT images may take one to five minutes, or even longer for more complex exams or complications with the scan and/or patient.

At step 760, images are generated. Based on the parameters provided by the post-processing protocol, generated images are generated based on the acquired images. This process may take one to five minutes, or even longer for larger and/or complex datasets, for example.

At step 770, the generated images are viewed. After the generated images have been generated, the operator may view the generated images to determine if the generated images appropriately cover the region of interest. Often, the generated images will not be ideal because the operator was not able to graphically prescribe them prior to the acquisition of the scan images.

At step 780, images are re-generated. When the generated images are incorrect, the operator may then adjust the post-processing parameters and re-generate the images.

FIG. 8 illustrates a flow diagram for a method 800 for 3D graphical prescription in accordance with an embodiment of the present invention. The method 800 includes the following steps, which will be described below in more detail. First, at step 810, a scan protocol is selected. Then, at step 820, a reference image is scanned. Next, at step 830, scan parameters may be graphically adjusted. At step 840, a post-processing protocol is selected. Then, at step 850, the post-processing parameters may be adjusted. Next, at step 860, the scan is confirmed. At step 870, images are generated. The method 800 is described with reference to elements of systems described above, but it should be understood that other implementations are possible.

First, at step 810, a scan protocol is selected. A scan protocol may, in part, configure an imaging system for a particular type of scan. A user may select a scan protocol based on, for example, an order specific to a patient regarding a region of the body to be scanned. For example, a patient may come to the imaging department of a medical facility with an order for a liver scan. A scan protocol may then be selected which configures the imaging system for the appropriate scan.

Then, at step 820, a reference image is scanned. An imaging component, such as an imaging system, scans one or more reference or scout images. The reference image(s) are presented to the operator on a display, for example. The reference image may be, for example, a CT scout image. In an embodiment, the reference image(s) may be acquired from an image management system such as PACS, for example. That is, the images used as reference images may have been acquired from a prior patient visit, for example, and stored in an information management system.

Next, at step 830, scan parameters may be graphically adjusted. The operator may graphically adjust the scan parameters, if necessary. The operator may graphically adjust the scan parameters by adjusting, for example, lines bounding the region to be scanned displayed on the reference image. The scan parameters may need to be adjusted if, for example, the parameters do not align the area to be imaged correctly for the specific patient.

A user may utilize a graphical prescription interface similar to, for example, the graphical prescription interfaces 300, 400, 500, described above, to adjust scan parameters. While graphical prescription interfaces 300, 400, 500 have been described in terms of prescribing an imaging volume for generating generated images, the graphical prescription interfaces 300, 400, 500 (and similar interfaces) may be utilized to adjust scan parameters. Scan parameters may be adjusted using a graphical prescription interface during scan setup, for example. That is, a graphical prescription interface similar to, for example, graphical prescription interface 300, may be used to specify a region of interest for scan images to be acquired. For example, an imaging volume prescribed by graphical prescription interface 300 may be used to configure an imaging system to scan an appropriate region of a patient's body. For example, in an MR modality, the imaging volume may be used to directly acquire the desired images. The graphical prescription interface may include symbology to allow the user to adjust and/or modify the imaging volume and/or region of interest for the scan images. The symbology may include control points, such as control points 340, described above, for example.

At step 840, a post-processing protocol is selected. The operator may select a post-processing protocol. Alternatively, the post-processing protocol may be specified as part of the scan protocol. For example, the post-processing protocol may prescribe an imaging volume to generate image slices for. As another example, the post-processing protocol may define an initial imaging volume. For example, a post-processing protocol may define an initial imaging volume around a particular organ of interest. The user may then, for example, use a graphical prescription interface (e.g., interface 300, described above) to adjust the initially defined imaging volume.

Then, at step 850, the post-processing parameters may be adjusted. Post-processing parameters may include, for example, an imaging volume from which generated images are to be generated. The generated images may be slices of the imaging volume, for example. A user may utilize a graphical prescription interface similar to, for example, the graphical prescription interfaces 300, 400, 500, described above, to adjust post-processing parameters. The graphical prescription interface may include symbology to allow the user to adjust and/or modify the imaging volume and/or region of interest for the generated images. The symbology may include control points, such as control points 340, described above, for example.

Next, at step 860, the scan is confirmed. The operator confirms the scan and an imaging component and/or an imaging system then acquires scan images. As discussed above, a graphical prescription interface, for example, a graphical prescription interface similar to interface 300, may be used to, at least in part, determine the scan images acquired. That is, an imaging component may acquire scan images based at least in part on an imaging volume prescribed by a graphical prescription interface.

At step 870, images are generated. Generated images may be generated based at least in part on the parameters provided by the post-processing protocol, for example. That is, the generated images are generated based at least in part on an imaging volume prescribed by a graphical prescription interface. The graphical prescription interface may be similar to the interface 300, described above, for example. In an embodiment, the generated images are generated by a processing component.

Generated images may be generated based at least in part on the acquired images, for example. In an embodiment, the generated images are generated based at least in part on an imaging volume prescribed by a graphical prescription interface and an acquired scan image. That is, a generated image may be generated based at least in part on an imaging volume and a scan image acquired by, for example, an imaging component.

In certain embodiments, a user may specify the orientation of a generated image using the graphical prescription interface. For example, the graphical prescription interface may include a control point, similar to control point 340, described above, that allows a user to designate which edge of the image slice in the imaging volume should be at the "top" of the generated image. In certain embodiments, the orientation of the generated images may be determined automatically. For example, the generated images may automatically be oriented so that the most anterior or superior portion of the slice is at the "top" of the generated images.

In certain embodiments, a reference image may be acquired by a first imaging component, as described above, for example. A scan image may then be acquired by a second imaging component. That is, a reference image may be acquired by one imaging system (e.g., CT scanner) and one or more scan images may be acquired by a second imaging system (e.g., MR scanner). For example, a patient may be registered with a CT scanner which acquires one or more reference images. On the same visit, or on a subsequent visit, the patient may be registered with an MR scanner and a user may utilize a graphical prescription interface (e.g., similar to interface 300, described above) on the MR scanner with the reference images from the CT scanner to prescribe an imaging volume for the MR scanner to acquire scan images for and/or to generate generated images based at least in part on acquired scan images from the MR scanner.

One or more of the steps of the method 800 may be implemented alone or in combination in hardware, firmware, and/or as a set of instructions in software, for example. Certain embodiments may be provided as a set of instructions residing on a computer-readable medium, such as a memory or hard disk, for execution on a computer or other processing device, such as, for example, a PACS workstation or image viewer.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for three-dimensional graphical prescription of an imaging volume, the system including:
   a display; and
   a graphical prescription interface configured to be displayed on the display, wherein the graphical prescription interface is configured to:
   present a two-dimensional reference image;
   present a three-dimensional representation of the imaging volume including a control point, wherein the three-dimensional representation of the imaging volume prescribes image slices to be generated;
   overlay at least a portion of the three-dimensional representation on the two-dimensional reference image; and
   allow an interaction with the control point to manipulate the three-dimensional representation of the imaging volume with respect to the two-dimensional reference image; and a processing component configured to:
communicate with the graphical prescription interface; and
generate the image slices according to the three-dimensional representation of the imaging volume.

2. The system of claim 1, wherein the graphical prescription interface is further configured to present the three-dimensional representation of the imaging volume on a plurality of two-dimensional reference images.

3. The system of claim 1, wherein the graphical prescription interface is further configured to present the three-dimensional representation of the imaging volume in an oblique position relative to the two-dimensional reference image.

4. The system of claim 1, wherein the graphical prescription interface is further configured to present a portion of the three-dimensional representation of the imaging volume outside a plane of the two-dimensional reference image.

5. The system of claim 1, further including an imaging component configured to:
communicate with the graphical prescription interface; and
scan an image according to the three-dimensional representation of the imaging volume.

6. A method for three-dimensional graphical prescription, the method including:
displaying a two-dimensional reference image on a display;
displaying a three-dimensional representation of an imaging volume including a control point, wherein a portion of the three-dimensional representation of the imaging volume is overlaid on the displayed two-dimensional reference image, wherein the three-dimensional representation of the imaging volume prescribes image slices to be generated;
allowing an interaction with the control point to manipulate the three dimensional representation of the imaging volume with respect to the two-dimensional reference image; and
generating the image slices according to the three-dimensional representation of the imaging volume.

7. The method of claim 6, further including determining automatically the orientation of the generated image.

8. The method of claim 6, further including acquiring a scan image at least in part by an imaging component.

9. The method of claim 8, wherein the acquired scan image is acquired by the imaging component according to the three-dimensional representation of the imaging volume.

10. A method for improving an imaging workflow, the method including:
displaying a two-dimensional reference image on a display;
presenting a three-dimensional representation of an imaging volume comprising a control point on the display, wherein a portion of the three-dimensional representation of the imaging volume is overlaid on the two-dimensional reference image, wherein the three-dimensional representation of the imaging volume prescribes image slices to be generated;
allowing an interaction with the control point to manipulate the three dimensional representation of the imaging volume with respect to the two-dimensional reference image;
acquiring a scan image according to the three-dimensional representation of the imaging volume; and
generating the image slices according to the three-dimensional representation of the imaging volume and the scan image.

11. The method of claim 10, wherein a portion of said presenting a three-dimensional representation of an imaging volume occurs during a scan setup.

12. The method of claim 10, further comprising acquiring the two-dimensional reference image by a first imaging component.

13. The method of claim 12, wherein said acquiring a scan image comprises acquiring the scan image by a second imaging component.

14. The method of claim 10, further comprising defining the three-dimensional representation of the imaging volume according to an imaging protocol.

15. A non-transitory computer-readable medium including a set of instructions for execution on a computer, the set of instructions including:
a display routine configured to:
display a two-dimensional reference image; and
overlay a three-dimensional representation of an imaging volume over the two-dimensional reference image, wherein the three-dimensional representation of the imaging volume includes a control point, wherein the three-dimensional representation of the imaging volume prescribes image slices to be generated;
an interaction allowance routine configured to:
allow an interaction with the control point; and
manipulate, in response to the interaction, the three-dimensional representation of the imaging volume with respect to the two-dimensional reference image; and
an image scanning routine configured to acquire a scanned image; and
an image generating routine configured to generate the image slices according to the three-dimensional representation of the imaging volume and the scanned image.

16. The set of instructions of claim 15, wherein said image scanning routine is further configured to acquire the scanned image according to the three- dimensional representation of the imaging volume.

* * * * *